United States Patent [19]

Mathew et al.

[11] Patent Number: 4,507,248

[45] Date of Patent: Mar. 26, 1985

[54] PREPARATION FROM HYDROXYLAMMONIUM SULFATE OF OXIMES AND HYDROXAMIC ACIDS VIA ALCOHOLIC HYDROXYLAMINE SOLUTION

[75] Inventors: Chempolil T. Mathew, Randolph; Harry E. Ulmer, Morristown, both of N.J.

[73] Assignee: Allied Corporation, Morris Township, Morris County, N.J.

[21] Appl. No.: 534,291

[22] Filed: Sep. 23, 1983

Related U.S. Application Data

[63] Continuation-in-part of Ser. No. 437,920, Nov. 1, 1982.

[51] Int. Cl.$^3$ .................... C07C 83/10; C07C 131/00
[52] U.S. Cl. ................... 260/500.5 H; 423/387; 423/545; 423/551; 564/259
[58] Field of Search ................. 564/259; 260/500.5 H

[56] References Cited

U.S. PATENT DOCUMENTS

| | | | |
|---|---|---|---|
| 2,346,665 | 4/1944 | Cupery | 260/500.5 H |
| 2,397,508 | 4/1946 | Rouault et al. | 260/500.5 H |
| 2,483,252 | 9/1949 | Tyron | 260/404 |
| 3,468,936 | 9/1969 | van der Burg | 260/500.5 H |
| 3,933,872 | 1/1976 | Hartlage | 260/500.5 H |
| 3,936,494 | 2/1976 | Lipowski | 260/500.5 H |
| 4,397,996 | 8/1983 | Chiklis et al. | 525/380 |

FOREIGN PATENT DOCUMENTS

| | | | |
|---|---|---|---|
| 1247284 | 8/1967 | Fed. Rep. of Germany | 423/387 |
| 513970 | 2/1976 | U.S.S.R. | 260/500.5 H |
| 925941 | 5/1982 | U.S.S.R. | 564/259 |

*Primary Examiner*—J. E. Evans
*Attorney, Agent, or Firm*—Alan M. Doernberg; Richard C. Stewart, II

[57] ABSTRACT

Solid hydroxylammonium sulfate is reacted with an alcohol solution of an alkali metal hydroxide or alkoxide to produce an alcoholic hydroxylamine liquid phase and a sulfate-containing solid phase. The liquid phase is used for further reactions such as oximations and hydroxamic acid production. The different bases behave differently with regard to suitable and preferable solvents and temperatures.

20 Claims, No Drawings

PREPARATION FROM HYDROXYLAMMONIUM SULFATE OF OXIMES AND HYDROXAMIC ACIDS VIA ALCOHOLIC HYDROXYLAMINE SOLUTION

This is a continuation-in-part of U.S. Ser. No. 437,920, filed Nov. 1, 1982.

BACKGROUND OF THE INVENTION

Hydroxylamine, usually in the form of salts such as hydroxylammonium sulfate, hydroxylammonium chloride or the like is widely used as a reagent for preparing various industrial, specialty and pharmaceutical chemicals. Reaction of a hydroxylamine reagent with ketones or aldehydes produce oximes. Other reactions of hydroxylamine reagents produce substituted hydroxylamines and hydroxamic acids. Where the organic starting material is either water-soluble or susceptible to an interfacial reaction with an aqueous solution of a hydroxylamine salt, either the chloride or sulfate salt may be used, and the sulfate salt is preferred because of its lower cost. Many products containing oxime or substituted hydroxylamine groups are not susceptible to production in aqueous media. Accordingly, such materials are normally prepared by reaction of solutions of hydroxylammonium chloride in organic solvents such as methanol with the organic precursor in the presence of sufficient base to neutralize the by-products HCl. Because hydroxylammonium sulfate (also called hydroxylamine sulfate) is not soluble in methanol, however, the cheaper sulfate reagent cannot be used to prepare these materials.

BRIEF DESCRIPTION OF THE INVENTION

A process has been discovered which enables solid hydroxylammonium sulfate to be used to provide hydroxylamine values in alcoholic solutions, and from such solutions various derivatives such as oximes. Accordingly, the present invention includes a process comprising the steps:

(a) reacting an alcoholic solution of a base selected from the group consisting of sodium hydroxide, potassium hydroxide, lithium hydroxide, ammonium hydroxide and the corresponding alkoxides of 1-5 carbons with solid hydroxylammonium sulfate, employing an alcohol of 1-3 carbons, a substantial absence of added water, a temperature not greater than about 30° C., a pressure and a time; said alcohol, temperature, pressure and time being sufficient to produce a liquid phase having at least 50% of the hydroxylamine values of the hydroxylammonium sulfate, (b) reacting the hydroxylamine values in the liquid phase with an organic reagent selected from the group consisting of aldehydes, ketones, acid chlorides and esters to form the corresponding product selected from the group consisting of aldoximes, ketoximes, and hydroxamic acids, (c) separating the solid phase comprising a sulfate salt corresponding to said base from the liquid phase containing hydroxylamine values or containing said corresponding product and (d) recovering from the liquid phase said product substantially free of water and sulfate impurities.

In the simplest form, the first step of the process produces an alcoholic solution of free hydroxylamine with little or no water content (depending upon the base used) and a by-product solid phase containing sulfate salts.

The organic reagent may be added before, during or after the reaction of step (a) and, if after step (a), then before or after the sulfate salt is removed in step (c). The separating step (c) may be conducted before, during or after the reacting step (b). The reaction of step (b) will not occur rapidly during step (a) even if the organic reagent is present because the conditions for rapid oximation (pH 5-8 and temperatures over 25° C.) are not present during step (a).

DETAILED DESCRIPTION OF THE INVENTION

Four materials used in the process of the present invention are a base, an alcohol solvent, hydroxylammonium sulfate and an organic reagent. The hydroxylammonium sulfate is normally in solid form, preferably divided up into relatively fine powder or crystals, and may be produced in a variety of processes including, especially, that described in U.S. Pat. No. 4,349,520 of Bonfield et al. (Sept. 14, 1982). The alcohol may be any alkanol of 1-3 carbons, and especially methanol or ethanol, but also isopropanol and propanol when the base is an alkoxide. The base may be sodium hydroxide, potassium hydroxide, lithium hydroxide, ammonium hydroxide or an alkoxide. Suitable alkoxides are those of 1-4 carbons such as methoxides, ethoxides, isopropoxides, propoxides and butoxides of sodium, potassium or lithium. It is contemplated, however, that for any particular base, not all alcohols are suitable. Furthermore, for any particular base, specified conditions of temperature and/or pressure may be necessary to achieve the desired conversion of at least about 50% of the hydroxylamine values from the solid hydroxylammonium sulfate to the liquid phase. The organic reagent is described below.

In the case of sodium hydroxide as base, any of the alcohols indicated above may be used as solvent. The preferred solvent for use with sodium hydroxide is methanol, with ethanol being slightly less preferred. It has been found that for both methanol and ethanol as solvent, the process of the present invention proceeds to higher conversions at lower temperatures. Thus the reaction temperature, while it may be as high as about 30° C., is preferably no greater than about 20° C. and more preferrably no greater than about 10° C. Comparative Example 3, below, illustrates the significantly lower yields obtained at 35°-40° C. compared to those obtained at 22°-25° C. (e.g., Example 2) and at 5°-10° C. (e.g., Example 1). The concentration of sodium hydroxide in methanol or ethanol is not critical, but it is preferred to operate as near to the solubility limit of sodium hydroxide in the alcoholic solvent as possible without creating so viscous a solution that agitation becomes difficult. Larger amounts of the solvent may also be used if tolerable in subsequent reactions. Various of the examples illustrate the use of relatively concentrated methanolic and ethanolic solutions of sodium hydroxide in the present process. The amount of sodium hydroxide should be at least that required to neutralize 50% of the hydroxylammonium sulfate reacted, preferably at least that necessary to neutralize all of the hydroxylammonium sulfate. It is contemplated that greater amounts of sodium hydroxide than that stoichiometrically required may be used and, as indicated in Example 9 below, such excess sodium hydroxide may increase the reaction rate without detracting from reaction yields.

Excess sodium hydroxide is normally to be used, however, only if the product alcoholic solution is to be used as a reagent in processes where more base would normally be charged at a later time. In other cases, the excess base can be neutralized before the solution is used further. Thus, the product solution can be formed at any desired pH such as from 5 to 12.

In using sodium hydroxide in ethanol as the solvent, lower temperatures are still preferred, with reaction below about 30° C., preferably below about 20° C. and more preferably no greater than about 10° C. being contemplated. It appears, however, that the reaction in ethanol is less temperature dependent than the reaction in methanol (see Examples 11 and 12 below).

Potassium hydroxide behaves quite differently from sodium hydroxide in the process of the present invention. First, methanol is not a suitable solvent for use with potassium hydroxide. As indicated in Comparative Examples 15 and 16 below, reaction of potassium hydroxide in methanol with hydroxylammonium sulfate produces extremely low yields either at 10° C. or at 22°–25° C. As indicated in Examples 17 and 18 below, however, potassium hydroxide in ethanol is a highly effective means of conducting the present process. These examples demonstrate that the reaction of potassium hydroxide in ethanol with hydroxylammonium sulfate proceeds at a slightly greater rate and to a slightly greater conversion at 22°–25° C. than at 5°–10° C. Accordingly, any temperature not greater than about 40° C. may be used with potassium hydroxide as the base, with temperatures of about 15° to about 25° C. being preferred. Temperatures above 40° C. should not normally be employed, however, since the product free hydroxylamine is likely to decompose significantly faster at such temperatures. As in the case of sodium hydroxide, potassium hydroxide may be used at any concentration and in any amount relative to the hydroxylammonium sulfate charged. Again, however, it is preferred in many cases to use a saturated or nearly saturated solution of potassium hydroxide in ethanol rather than a dilute solution. It is also preferred to use, relative to the stoichiometric amount of potassium hydroxide, at least that needed to neutralize 50% of the hydroxylammonium sulfate, preferably at least that necessary to neutralize all of the hydroxylammonium sulfate. Excesses of potassium hydroxide may also be used.

Lithium hydroxide, as a base in the present invention, may be used with methanol or ethanol. The reaction appears to proceed to slightly higher conversions at higher temperatures, as indicated by Examples 13 and 14 below. Nevertheless, any temperature up to about 40° C. may be used, with a range of about 10° to about 40° C. being preferred, and a range of about 15° to about 25° being more preferred. The reaction of lithium hydroxide in methanol appears to proceed at a slower rate and/or to a lower final conversion than either the reaction of sodium hydroxide in methanol or ethanol or the reaction of potassium hydroxide in ethanol. The above comments relating to concentration of base in the alcohol and to amounts of base relative to hydroxylammonium sulfate made in respect to sodium hydroxide and potassium hydroxide apply equally to lithium hydroxide.

While isopropanol or propanol may be used as solvents with NaOH, KOH or LiOH, the limited solubilities of these hydroxides and of the product hydroxylamine in these solvents makes these embodiments less preferred to those described above.

Ammonium hydroxide, as a base, may be used with any of the lower alcohols in a manner similar to that employed with lithium hydroxide. The term "ammonium hydroxide" is intended to include ammonia plus some amount of water, such as equimolar amounts of ammonia and water, or half or twice the equimolar amount of water. Using ammonia without any water is not considered satisfactory, based on the poor yields shown in comparative Examples 20–24, below.

In using sodium hydroxide, potassium hydroxide or lithium hydroxide, pressure is not a critical factor since neither the base nor the solvent is very volatile. Only when ammonia is used, is pressure at all a factor, and even then atmospheric or even pressures below atmospheric may be used, but pressures at or above atmospheric pressure are preferred, and atmospheric pressure is more preferred.

Alkoxides such as sodium methoxide, ethoxide, isopropoxide, propoxide, butoxide and pentylate may be used in place of the hydroxides, having the advantage of not producing water as by-product. Therefore, when a substantially water-free hydroxylamine solution is desired, these more expensive alkoxide bases should be used. Normally, the solvent will correspond to the anion (e.g., sodium methoxide in methanol), but mixed systems (e.g., sodium butoxide in methanol) may be used if the solvent later present (after the hydroxylamine-consuming reaction) is not to be recovered and recycled or can be distilled. While the anion may be larger than three carbons, the solvent is normally a 1–3 carbon alkanol (and is preferably methanol or ethanol) because free hydroxylamine is more soluble in these lower alkanols.

In similar fashion, the alkoxides of lithium and potassium may be used, except that potassium alkoxides would normally not be used with methanol as solvent.

Alkoxides are more expensive than hydroxides and are, therefore, normally not used unless the 3% or so water in the product solution of the above reactions of hydroxides cannot be tolerated for a particular use. The present invention, using alkoxides, still makes available the use of cheaper hydroxylammonium sulfate for such water-sensitive uses.

In each case, one preferred mode of conducting the reaction is to first dissolve (or slurry) the base in the alcohol and then react the alcoholic solution with hydroxylammonium sulfate. As illustrated by Examples 1 and 8, below, essentially identical results can be achieved either by adding the solid hydroxylammonium sulfate to the alcoholic solution or by adding the alcoholic base to the solid hydroxylammonium sulfate. Furthermore, it is contemplated that the two may be mixed in any conventional batch or continuous process scheme normally used to react a solid with a liquid. A less preferred method of conducting the present invention is to mix the base (solid or gas) with the hydroxylammonium sulfate first, and then to add the alcohol. This scheme is less preferred because the process of dissolving the base in the alcohol (which is required before the reaction can occur) is normally an exothermic reaction. Since high temperatures are generally not required (and in the case of sodium hydroxide are preferably avoided), it is desirable that the act of dissolving base in alcohol be conducted first, that the alcohol solution be cooled and that the cooled alcoholic solution be reacted with the hydroxylammonium sulfate. Another less preferred method is to add the base slowly to hydroxylammonium sulfate slurried in alcohol.

Once the reaction between alcoholic base and hydroxylammonium sulfate is complete, or while it is proceeding, the alcoholic solution containing hydroxylamine values may be further reacted with an organic reagent such as an aldehyde or ketone. In one mode, this reaction is conducted after separating the by-product sulfate (e.g., sodium sulfate) from the alcoholic hydroxylamine solution. Thus, as illustrated in the Examples below, the alcoholic hydroxylamine solution is reacted with methyl ethyl ketone to produce methyl ethyl ketone oxime. Such reaction may be conducted at the pH normally used for the reaction involved, with pH between about 5 and about 8 used to convert ketones or aldehydes to oximes. It is contemplated that such further reaction of hydroxylamine may be conducted prior to separating the by-product sulfate, such as by having a ketone present in or added with the alcoholic sodium hydroxide solution or added after the free base is liberated but before the sulfate salt is filtered out. In such case, as free hydroxylamine becomes available in the alcoholic solution, it reacts with ketone or aldehyde (provided that the proper pH and temperature is reached).

The various modes of reaction can be illustrated for acetone, for example, which like most carbonyl compounds reacts rapidly with hydroxylamine values only at pH 5–8 and temperatures of at least about 25° C.

Mode 1

Step 1: Mix NaOH, MeOH, hydroxylammonium sulfate (HS) and acetone and stir at 5° C. for approximately 5 hours.
Step 2: Adjust to pH about 8, raise temperature to 30° C. and stir for 2 hours.
Step 3: Filter out $Na_2SO_4$
Step 4: Evaporate solvent and recover acetone oxime crystals.

Mode 2

Same as Mode 1 with step 3 after adjusting to pH about 8 and before raising temperature to 30° C.

Mode 3

Step 1: Mix NaOH, MeOH and HS and stir at 5° C. for about 5 hours.
Step 2: Add acetone, adjust pH to about 8, raise temperature to 30° C. and stir for about 2 hours.
Step 3: Filter out $Na_2SO_4$.
Step 4: Evaporate solvent and recover acetone oxime crystals.

Mode 4

Same as Mode 3 with step 3 after adjusting to pH 8 and before raising temperature.

Modes 1 and 3, wherein the $Na_2SO_4$ is filtered out last are preferred for three reasons: first, the presence of $Na_2SO_4$ can help dry the liquid phase, even of by-product water from the oximation reaction of step (b); second, any grit or other solids entering during any reaction step will be present in the by-product sulfate salt rather than in the organic product crystals and, third, sulfate removal may be more complete with a larger and less polar organic liquid layer.

Organic reactants suitable for the present process include any that will react with the hydroxylamine values in the liquid phase after reaction step (a), with or without suitable pH and temperature adjustments. Suitable aldehydes which, on reaction, produce aldoximes, include formaldehyde, acetaldehyde, proprionaldehyde, benzaldehyde, hydroxybenzaldehyde (such as salicylaldehyde) butyraldehyde and isobutyraldehyde. Suitable ketones which, on reaction, produce ketoximes include acetones, butanone (MEK), 3-pentanone (diethylketone), benzoin, acetophenone, benzophenone, o-hydroxybenzophenone and o-hydroxyacetophenone. Benzoquinonedioxime can be produced by the present process from p-nitrosophenol. Hydroxamic acids can be produced by the present process from esters and acid chlorides such as ethyl acetate and benzoyl chloride.

The step of removing the by-product solid sulfate from the alcoholic solution containing hydroxylamine values may be carried out using any conventional technique for separating a solid from a liquid. Centrifugation, filtration, decantation and other conventional engineering steps are included. It is preferred that the recovered solid be washed with a solvent (such as the alcohol used for the solution) to remove adhered hydroxylamine-containing alcohol. Thereafter the solid may be dried, washed or recrystallized, treated in other ways to recover unreacted hydroxylammonium sulfate, or disposed of as initially separated.

The product (oxime or hydroxamic acid) may be subjected to further reaction in the alcohol solvent or may be recovered therefrom by conventional techniques such as distillation, evaporative crystallization or precipitation with added non-solvent.

The present invention is illustrated by the following Examples, which are not intended to limit the invention, Examples 1, 6 and 7 being set forth in full, certain others being tabulated:

EXAMPLE 1

A solution of methanolic sodium hydroxide was prepared by mixing sodium hydroxide pellets (17.2 g; 0.43 mol) with absolute methanol (150 mL) in a 250 mL Erlenmeyer flask.

In the meantime a 500 mL 3-necked flask was fitted with a thermometer, dropping funnel and nitrogen inlet (inert atmosphere) and a magnetic stirring bar (PTFE-coated, 1½ inches or 3.8 cm long) was placed in it. Solid hydroxylamine sulfate (35 g); 0.213 mol) was placed in the flask with methanol (50 mL) and the flask was placed in an ice-water bath over a stir plate. With vigorous stirring, the methanolic NaOH solution was added slowly (over 5 minutes) using the dropping funnel, maintaining the reaction mixture temperature below 10° C. After the addition was complete, stirring was continued for 1½ hours more with cooling (5°–10° C.). A white slurry resulted and this was filtered over a Buchner funnel and the cake was washed with more methanol (25 mL). The clear and colorless filtrate (pH 12.5) was analyzed for free hydroxylamine by mixing with known excess of methyl ethyl ketone (MEK) (40 g) and adjusting the pH to 7 with concentrated $H_2SO_4$ (2.5 g). Methyl ethyl ketoxime formed was determined by gas chromatography to correspond to free hydroxylamine (87.4% yield).

The white filter cake (34.2 g) of sodium sulfate was analyzed for remaining hydroxylamine sulfate by dissolving in water (150 mL) and mixing with excess of MEK (40 g) and titrating with 50% NaOH solution (3.9 g) to pH 7. The amount of hydroxylamine sulfate left in the cake represented 11.4% of the total.

EXAMPLE 6

The same equipment as in Example 1 was used. A total of 200 mL of methanol was used to slurry hydroxylamine sulfate (35 g; 0.213 mol) with NaOH (17.2 g; 0.43 mol). The reaction was conducted below 10° C. using ice water bath for 4 hours with vigorous stirring.

The filtrate, when analyzed in the usual manner (gas chromatography), showed 91.6% yield of free hydroxylamine. The cake required 2.6 g of 50% NaOH representing 7.6% of hydroxylamine sulfate.

EXAMPLE 7

Sodium hydroxide pellets (103.2 g; 2.58 mol) were dissolved in absolute methanol (750 mL) and added slowly (15 minutes) to a stirred slurry of hydroxylamine sulfate (210 g; 1.28 mol) with methanol (228 mL) placed in a 2 liter, 3-necked flask fitted with thermometer, dropping funnel and an overhead glass stirrer with three inch long PTFE paddle. A five-eighths inch wide PTFE baffle was also introduced into the liquid to provide good agitation. The temperature during the addition and subsequent stirring (4 hours) was maintained at 5° C. using a thermostated bath.

The white slurry at the end of stirring was filtered and the cake washed with more methanol. The total filtrate (845.5 g) was analyzed by gas chromatography after conversion to MEK oxime by mixing with MEK and adjusting pH to 7 (from pH 12.9) using concentrated $H_2SO_4$ (21.0 g). Yield 82.1% hydroxylamine.

The wet cake (208.5 g) was dissolved in water (900 g) and mixed with MEK (200 g) and then neutralized with 50% NaOH solution (35.8 g). The leftover hydroxylamine sulfate in the cake correspond to 17.3% of the total sulfate used.

Others of Examples 1–24 are set forth in greater detail in U.S. Ser. No. 437,920, filed Nov. 1, 1982, the disclosure of which is incorporated by reference. Examples 1–24 are summarized in Table 1, below:

TABLE 1

| Example | Base | Solvent | Temperature | Time (hours) | Yield (%) | % In Cake |
|---|---|---|---|---|---|---|
| 1 | NaOH | MeOH | 5–10° C. | 1.5 | 87.4% | 11.4% |
| 2 | NaOH | MeOH | 22–25° C. | 2 | 71.2% | — |
| C3 | NaOH | MeOH | 35–40° C. | 1.5 | 18.8% | 76.5% |
| 4 | NaOH | MeOH | 5–10° C. | 6 | 90.7% | 0.9% |
| 5 | NaOH | MeOH | 10° C. then 22° C. | 6 12 | 80.5% | trace |
| 6 | NaOH | MeOH | <10° C. | 4 | 91.6% | 7.6% |
| 7* | NaOH | MeOH | 5° C. | 4 | 82.1% | 17.3% |
| 8** | NaOH | MeOH | 5–10° C. | 1.5 | 86.6% | 10.4% |
| 9* | NaOH | MeOH | 7–10° C. | 1 | 78.3% | 12.2% |
| 10** | NaOH | MeOH | 5–10° C. | 2 | 70.8% | 27.9% |
| 11 | NaOH | EtOH | 5–10° C. | 3 | 88.3% | 4.7% |
| 12 | NaOH | EtOH | 22–25° C. | 3 | 89.1% | 2.9% |
| 13 | LiOH*** | MeOH | 10° C. | 1.5 | 45.8% | 42.6% |
| 14 | LiOH*** | MeOH | 22–24° C. | 3 | 53.8% | 13.1% |
| C15 | KOH | MeOH | 10° C. | 3 | <1% | almost all |
| C16 | KOH | MeOH | 22–25° C. | 1 | <5% | almost all |
| 17 | KOH | EtOH | 22–25° C. | 3 | 77.9% | 16.6% |
| 18 | KOH | EtOH | 5–10° C. | 3 | 70.0% | 24.1% |
| 19 | $NH_3$ | MeOH | about 20° C. | 3 | 46.7% | 42.4% |
| C20** | $NH_3$ | MeOH | 5–10° C. | 3 | 17.1% | 78.5% |
| C21** | $NH_3$ | MeOH | 10° C. | 3 | 10.0% | 82.8% |
| C22** | $NH_3$ | MeOH | 40–50° C. | 2 | 5.7% | 84.0% |
| C23** | $NH_3$ | EtOH | 19° C. | 3 | 13.9% | 76.7% |
| C24** | NaOH | $Et(OH)_2$ then | 20–25° C. 30° C. | 2 1 | 7.4% | 75.3% |

The indicated examples used larger molar amounts of at least one reagent and/or larger volumes of alcohol solvent as follows:

| Example | Base (mol) | Solvent | Total Alcohol | HS (mol) |
|---|---|---|---|---|
| 7 | NaOH 2.58 | | MeOH 978 mL | 1.28 |
| 9 | NaOH 0.86 | | MeOH 288 mL | 0.213 |

**The indicated examples used other variations from Example 1 as follows:
Example 8 - solid HS was added to 0.43 mol of NaOH dissolved in 200 mL methanol over 20 minutes with stirring.
Example 10 - 0.43 mol of NaOH was dissolved in 150 mL of methanol and 7.5 mL of water;
Example 19 - ammonia gas bubbled into a mixture of 0.213 mol HS, 200 mL MeOH and 1.0 mL water. Repeated until pH stayed above 9.0;
Comparative Examples 20–22 - 11.6% $NH_3$ solution (10.2 g $NH_3$) in MeOH added to 0.213 mol HS in 100 mL MeOH. Autoclave used for Comparative Examples 21 and 22.
Comparative Example 23 - 5.7% $NH_3$ solution in ethanol (8.55 g $NH_3$) added to 0.213 mol HS in 50 mL ethanol.
***$LiOH \cdot H_2O$

EXAMPLE 25

Preparation of Benzophenone Oxime

Sodium hydroxide pellets (103 g; 2.58 mol) were dissolved with stirring in absolute methanol (750 mL) at ambient temperature. The solution was placed in a dropping funnel placed on a 3-neck, 2 liter, baffled round bottom flask fitted with thermometer and an overhead agitator. In the flask was placed solid hydroxylamine sulfate (210 g; 1.28 mol) mixed with absolute methanol (450 mL). With vigorous agitation and cooling in an ice bath (0°–5° C.), the methanolic sodium hydroxide solution was added over about 30 minutes. The white slurry was stirred further with cooling for 5 hours more and pH adjusted from pH 12 to 9 using concentrated $H_2SO_4$ (12 g) and filtered. The filter cake of sodium sulfate was washed on the funnel with absolute methanol (50 mL). The total filtrate (1280 mL, clear, colorless solution) was analyzed for free hydroxylamine base and found to contain 5.27 g/100 mL solution.

A 500 mL 3-neck flask was fitted with thermometer, dropping funnel and nitrogen blanket. Benzophenone (36.5 g; 0.2 mol) in absolute methanol (100 mL) was placed in the flask and cooled in an ice bath (5° C.) with stirring using a magnetic stirring bar. Hydroxylamine solution (133 mL) was slowly added and after completion of addition (15 minutes), the mixture was heated at reflux (65° C.). pH 8.6. After a total of 18 hours of heating under reflux, it was cooled and transferred to a 500 mL round bottom flask and concentrated on a rotovap. On cooling in ice bath, it was filtered and benzophenone oxime was collected as white crystalline solid (32.5 g; 89% yield). Purity, >97%.

The product was kept sealed in a clear jar purged with nitrogen and it remained stable indefinitely.

EXAMPLE 26

Preparation of Benzophenone Oxime

Benzophenone (182 g; 1.0 mol) mixed with absolute methanol (400 mL) was placed in a 2-liter 3-neck flask (baffled) fitted with over-head stirrer. To the solution was added hydroxylamine sulfate (120 g; 0.73 m) and maintained vigorously stirred with cooling in ice bath (5° C.). A solution of sodium hydroxide pellets (60 g; 1.50 mol) in absolute methanol (400 mL) was then added slowly with continued agitation. After stirring for 6 hours with cooling, it was heated under reflux (67° C.). pH of the mixture was 11.2. Heating at reflux continued for a total of 12 hours and the solution filtered while still hot.

The clear filtrate was then further concentrated on the rotovap and cooled and filtered to collect benzophenone oxime (174 g; 88.3%). Purity: about 98%. Major impurity was benzophenone (gas chromatography).

The oxime sample remained stable for over a long period of time in a bottle purged with nitrogen and tight-sealed with plastic tape. On the other hand, a portion of the same sample kept in a similar bottle loosely closed turned brown and eventually to a liquid after about 10 days.

EXAMPLE 27

Preparation of Acetone Oxime

A 2 liter 3-neck flask with baffles was fitted with over-head stirring and thermometer and dropping funnel. Hydroxylamine sulfate (210 g; 1.28 mol) was placed in the flask mixed with absolute methanol (400 mL) and stirred vigorously with cooling in ice bath (5° C.). A solution of sodium hydroxide pellets (103 g; 2.58 mol) in absolute methanol (800 mL) was added from the dropping funnel slowly over 30 minutes. Stirring with cooling was continued over 5 hours. pH of the white slurry was adjusted to 6.5 using Conc. $H_2SO_4$ (5.8 g). Acetone (148.5 g; 2.56 mol) was added to the slurry slowly and stirring continued for 1 hour more.

The white slurry was filtered to remove sodium sulfate and the clear filtrate concentrated on the rotovap. White crystalline solid of acetone oxime was collected (168 g) as the first crop. The colorless solution furnished a second crop of acetone oxime crystals (13.5 g) on further evaporation and cooling. Total yield 97.4%. Purity >99% (gas chromatography).

EXAMPLE 28

Preparation of Acetophenone Oxime

In a 500 mL 3-neck flask was placed solid hydroxylamine sulfate (28 g; 0.17 mol) and absolute methanol (100 mL) was added to it. The slurry was stirred vigorously using a magnetic bar over a stir plate and a solution of sodium hydroxide pellets (14 g; 0.35 mol) in absolute methanol (175 mL) was then added slowing with cooling in ice bath (<5° C.). At the completion of addition of the solution, acetophenone (40 g; 0.33 mol) was added and stirring in the cold was continued for 5 hours. Concentrated $H_2SO_4$ (1.8 g) was added to adjust the pH of the solution to 6.5. Methanol (50 mL) was added to the slurry and the mixture heated (40° C.) for 2 hours and then filtered hot. The clear filtrate (colorless) was concentrated under reduced pressure and crystalline acetophenone oxime was collected after cooling and filtration. Yield, 40.5 g (90.8%). Purity >98% of isomeric mixture.

EXAMPLE 29

Preparation of Acetone Oxime

In a 100 mL Erlenmeyer flask furnished with a magnetic stirring bar was placed a methanolic hydroxylamine solution (50 mL; 4.68 g $NH_2OH$ per 100 mL) prepared as in Example 25. Cooling in ice bath, the temperature was maintained at about 10° C. and acetone (4 g; 0.069 mol) was added slowly with stirring. After stirring for 15 minutes more without cooling the clear, colorless solution (pH 7.3) was placed in a 200 mL round bottom flask and carefully evaporated (rotovap) and a crystalline solid collected (6.2 g). Gas chromatography showed that it was virtually pure acetone oxime. Yield 97.7%.

EXAMPLE 30

A 500 mL 3-necked flask was fitted with a thermometer, reflux-condenser and drying tube. Freshly cut sodium (10.0 g; 0.435 mol) was placed in the flask and absolute methanol (175 mL) was carefully added with cooling. After the sodium was completely dissolved in methanol forming a clear solution of sodium methoxide, solid hydroxylamine sulfate (35 g; 0.213 mol) was added with cooling over 2 minutes. No significant exotherm was noticed. The mixture was stirred with cooling (10° C.) in ice-water bath using a magnetic stirring bar over a stir plate for one hour. Subsequently, cooling was removed and vigorous stirring continued at ambient temperature for 2 hours more. By this point a white slurry had formed, and this was filtered and the cake washed using more methanol. The total filtrate (162 g) was analyzed potentiometrically and found to contain hydroxylamine corresponding to 87.5% yield. The filtrate was virtually free of water (<0.5% $H_2O$).

The white solid (32 g) was dissolved in water and analyzed for unused hydroxylamine sulfate (1.6%).

The solution (filtrate) can be used to make oximes or hydroxamic acids, and would be particularly useful where the starting material or product is water-sensitive, as in the conversion of benzophenone to benzophenone oxime or the conversion of acid chlorides such as benzoyl chloride to hydroxamic acids such as benzohydroxamic acid.

COMPARATIVE EXAMPLE 31

In a 500 mL 3-necked flask was fitted with thermometer, reflux condenser, and drying tube was placed absolute methanol (100 mL) and freshly-cut potassium (8.4 g; 0.215 mol) was added piece-by-piece with cooling in ice-bath and a clear solution of potassium methoxide in methanol was produced. To this solution was added with vigorous stirring crystalline hydroxylamine sulfate (17.5 g; 0.107 mol) and stirring was continued at ambient temperature for 3 hours. No noticeable change (no milkiness) was found to be developing.

The slurry was filtered and the filter cake was washed with more methanol. The total filtrate (125 g) was analyzed potentiometrically and found to contain virtually no hydroxylamine (<0.3% yield). The crude filter cake (18 g) which appeared crystalline (similar to the starting hydroxylamine sulfate) was dissolved in water (75 mL) and analyzed and found to contain over 95% of the starting hydroxylamine sulfate.

This comparative example shows the low yields with potassium methoxide in methanol (analogous to potassium hydroxide in methanol in C15 and C16. It is expected that potassium ethoxide in ethanol (analogous to potassium hydroxide in ethanol in 17 and 18) would give high yields of dry ethanolic hydroxylamine that could be used for making oximes and hydroxamic acids.

What is claimed is:

1. A process comprising the steps of:
    (a) reacting an alcoholic solution of a base selected from the group consisting of sodium hydroxide, potassium hydroxide, lithium hydroxide, ammonium hydroxide and the corresponding alkoxides of 1-5 carbons with solid hydroxylammonium sulfate, employing an alcohol of 1-3 carbons, a substantial absence of added water, a temperature not greater than about 30° C., a pressure and a time; said alcohol, temperature, pressure and time being sufficient to produce a liquid phase having at least 50% of the hydroxylamine values of the hydroxylammonium sulfate, (b) reacting the hydroxylamine values in the liquid phase with an organic reagent selected from the group consisting of aldehydes, ketones, acid chlorides and esters to form the corresponding product selected from the group consisting of aldoximes, ketoximes, and hydroxamic acids, (c) separating the solid phase comprising a sulfate salt corresponding to said base from the liquid phase containing hydroxylamine values or containing said corresponding product, and (d) recovering from the liquid phase said product substantially free of water and sulfate impurities.

2. The process of claim 1 wherein said base is sodium hydroxide.

3. The process of claim 2 wherein the alcohol is methanol.

4. The process of claim 2 wherein the alcohol is ethanol.

5. The process of claim 2 wherein the reaction is conducted at a temperature not greater than about 30° C.

6. The process of claim 3 wherein the reaction is conducted at a room temperature not greater than about 20° C.

7. The process of claim 6 wherein the reaction is conducted at a temperature not greater than about 10° C.

8. The process of claim 1 wherein said base is potassium hydroxide.

9. The process of claim 8 wherein the alcohol is ethanol.

10. The process of claim 9 wherein the reaction is conducted at a temperature between about 10° C. and about 40° C.

11. The process of claim 10 wherein the reaction is conducted at a temperature between about 15° C. and about 25° C.

12. The process of claim 1 wherein said base is lithium hydroxide.

13. The process of claim 1 wherein said base is an alkoxide.

14. The process of claim 13 wherein the base is sodium methoxide and the solvent is methanol.

15. The process of claim 13 wherein the base is sodium ethoxide or potassium ethoxide and the solvent is ethanol.

16. The process of claim 1 wherein said separating step (c) comprises separating a free hydroxylamine solution in alcohol of pH between about 5 and about 8 from a solid phase comprising said sulfate salt corresponding to said base.

17. The process of claim 1 wherein hydroxylamine values in said liquid phase are reacted with the organic reagent prior to separating the liquid phase from the solid phase containing sulfate salt corresponding to said base.

18. The process of claim 17 wherein said product is an oxime.

19. The process of claim 1 wherein said product is an oxime.

20. The process of claim 1 wherein said product is a hydroxamic acid.

* * * * *